(12) United States Patent
Schnabel et al.

(10) Patent No.: US 8,888,754 B2
(45) Date of Patent: *Nov. 18, 2014

(54) ABSORBENT ARTICLE HAVING A COLOR-PIGMENTED AND PRINTED BACKSHEET

(71) Applicant: The Procter & Gamble Company, Cincinnati, OH (US)

(72) Inventors: Martin Schnabel, Frankfurt (DE); Radhakrishnan Janardanan Nair, Kobe (JP); Kesyin Fugger Hsueh, Singapore (SG)

(73) Assignee: The Procter & Gamble Company, Cincinnati, OH (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/104,384

(22) Filed: Dec. 12, 2013

(65) Prior Publication Data

US 2014/0100543 A1     Apr. 10, 2014

Related U.S. Application Data

(63) Continuation of application No. 10/730,438, filed on Dec. 8, 2003, now Pat. No. 8,613,736.

(60) Provisional application No. 60/435,625, filed on Dec. 20, 2002.

(51) Int. Cl.
    *A61F 13/15*     (2006.01)
(52) U.S. Cl.
    USPC ................................ 604/385.01; 604/385.23
(58) Field of Classification Search
    USPC ........................ 604/385.04, 385.01
    See application file for complete search history.

(56) References Cited

U.S. PATENT DOCUMENTS

| | | | |
|---|---|---|---|
| 3,003,388 A | 10/1961 | Hunter et al. | |
| 3,972,854 A | 8/1976 | Costolow | |
| 4,249,532 A | 2/1981 | Polansky et al. | |
| 4,438,169 A | 3/1984 | Daniels et al. | |
| 4,840,846 A | 6/1989 | Ejima et al. | |
| 5,133,707 A | 7/1992 | Rogers et al. | |
| 5,236,645 A | 8/1993 | Jones | |
| 5,458,590 A | 10/1995 | Schleinz et al. | |
| 5,575,782 A | 11/1996 | Hasse et al. | |
| 5,612,118 A | 3/1997 | Schleinz et al. | |
| 5,695,855 A | 12/1997 | Yeo et al. | |
| 5,897,541 A | 4/1999 | Uitenbroek et al. | |
| 6,075,178 A | 6/2000 | La Wihelm et al. | |
| 6,096,412 A | 8/2000 | McFarland et al. | |
| 6,136,427 A | 10/2000 | Boaz | |
| 6,297,424 B1 | 10/2001 | Olson et al. | |
| 6,368,667 B1 | 4/2002 | Burazin et al. | |
| 6,477,948 B1 | 11/2002 | Nissing et al. | |
| 6,497,691 B1 | 12/2002 | Bevins et al. | |
| 6,528,565 B1 | 3/2003 | Russell | |
| 6,719,742 B1 | 4/2004 | McCormack et al. | |
| 6,949,689 B2 | 9/2005 | Noda et al. | |
| 8,613,736 B2 * | 12/2013 | Schnabel et al. | 604/385.01 |
| 2002/0112832 A1 | 8/2002 | Burazin et al. | |
| 2003/0044578 A1 | 3/2003 | Nissing | |
| 2004/0058130 A1 | 3/2004 | Nissing | |

FOREIGN PATENT DOCUMENTS

| | | |
|---|---|---|
| EP | 1 247 508 A2 | 10/2002 |
| EP | 1 252 873 A2 | 10/2002 |
| JP | 08-019570 A | 1/1996 |
| JP | 2000-000026 A | 1/2000 |
| JP | 2002-153503 A | 5/2002 |
| WO | WO 93-19714 A1 | 10/1993 |
| WO | WO 96-10380 A2 | 4/1996 |
| WO | WO 99-32164 A1 | 7/1999 |
| WO | WO 99 60973 A1 | 12/1999 |
| WO | WO 00-07426 A2 | 2/2000 |
| WO | WO 00-38915 A1 | 7/2000 |
| WO | WO 02-07661 A2 | 1/2002 |

OTHER PUBLICATIONS

Online encyclopedia article, "Halftone", accessed Feb. 22, 2008, http://en.wikipedia.org/wiki/Halftone.

* cited by examiner

*Primary Examiner* — Jacqueline F. Stephens

(74) *Attorney, Agent, or Firm* — William E. Gallagher

(57) ABSTRACT

The present invention relates to disposable absorbent articles such as diapers and adult incontinence products, which collect and retain urine and fecal material deposited thereon by the wearer. The disposable absorbent articles of the present invention comprise a color-pigmented backsheet, which further comprises visually discernible ornamental designs printed thereon.

21 Claims, No Drawings

ABSORBENT ARTICLE HAVING A COLOR-PIGMENTED AND PRINTED BACKSHEET

CROSS-REFERENCE TO RELATED APPLICATION

This application claims the benefit of U.S. Provisional Application No. 60/435,625, filed Dec. 20, 2002.

FIELD OF THE INVENTION

The present invention relates to disposable absorbent articles such as diapers and adult incontinence products, which collect and retain urine and fecal material deposited thereon by the wearer. The disposable absorbent articles of the present invention comprise a color-pigmented backsheet, which further comprises visually discernible ornamental designs printed thereon.

BACKGROUND OF THE INVENTION

In short-period usage absorbent articles such as daytime diapers, light, thin and flexible materials are especially desirable to provide improved freedom of movement and increased comfort for the wearer. Therefore, it is preferred to apply materials like polymeric films or nonwoven webs with very low basis weights.

However, a drawback of a disposable article using very low basis weight materials is that these materials have an increased tendency to be translucent. It is difficult to manufacture thin materials, which provide a desired degree of opacity, because only a limited amount of whiteners, such as titanium dioxide, can be added without receiving materials, which are brittle and tend to disintegrate easily.

The problem of translucency in light, thin, and flexible absorbent articles is further increased by the fact, that such articles may comprise regions with only very few overlying layers of material. For example, in a diaper the use of a thin and relatively small absorbent core results in a relatively large area in the front and/or rear waist region of the diaper, which only comprises a topsheet and a backsheet overlying each other.

While light, thin and flexible diapers with improved freedom to move are highly appreciated by the consumer, translucency is usually disliked by the wearer or caretaker. The skin of the wearer is shining through the diaper in some areas and moreover, the structural features inside the diaper, like for example elastics or parts of the absorbent core, can be seen from the outside due to thin covering materials. Hence, the diaper tends to get a rather patchy appearance.

The above-said becomes even more problematic, when the diaper is soiled and the stains of the absorbed exudates shine through, due to a thin absorbent core and a light, translucent backsheet.

It is thus an objective of the present invention to provide a light, thin and flexible absorbent article with an improved outer appearance without the need to employ economically unattractive materials.

It is a further objective of the present invention to provide a light, thin absorbent article, which looks like an undergarment, especially for use as a daytime diaper.

Color-printed materials for use in absorbent articles are well known in the art:

WO 99/60973 filed May 28, 1998 entitled "Clothlike, breathable backsheet with multicolored graphics for disposable absorbent article" discloses absorbent articles with a backsheet comprising a microporous polymer film printed with multicolored graphics and a nonwoven material laminated to the film. The microporous film has a "b" value from 0.0 to 0.5 and less than 4% thermal shrinkage at 50° C. and 50% relative humidity for one week.

WO 99/32164 filed Dec. 19, 1997 entitled "Disposable absorbent articles comprising microporous polymer films with registered graphics" relates to absorbent articles with a backsheet comprising a microporous film printed with a registered graphic and comprising by weight 30-60% polyolefin and 40 to 80% calcium carbonate. The microporous film has a "b" value from 0 to 5 and less than 2% thermal shrinkage at 50° C. and 50% relative humidity for one week.

One drawback with printing is, that printing large areas of the backsheet becomes expensive and thus, is not economically attractive. Moreover, to receive intense colors, high amounts of ink have to be applied, which—besides raising expenses—may lead to the rubbing-off of ink during use of the disposable article.

Besides printing, other techniques to improve the appearance of materials for use in absorbent articles have been developed:

WO 93/19714 filed Mar. 22, 1993 entitled "Multilayer film exhibiting an opaque appearance" discloses a multilayer film comprising two outer layers and a central polymeric layer. The central layer has high concentrations of pigments or other fillers to increase the masking ability. The central layer may be whitened or colored. However, due to the number of layers, the multiplayer film is rather thick and thus not very suitable for use in a light, flexible diaper.

WO 96/10380 filed Aug. 4, 1995 entitled "Laminate material and absorbent garment comprising same" refers to a laminate material with a first layer having opaque areas, transparent areas and a coloration and a second layer having a different coloration than the first layer. The coloration of the second layer is visible through the transparent areas of the first layer to a greater extent than through the opaque areas of the first layer.

EP 1 252 873 A2 and EP 1 247 508 A2 both filed Apr. 4, 2002 and both entitled "Discreet absorbent articles" disclose absorbent articles comprising a pigmented cover, a pigmented apertured transfer layer and a pigmented backsheet, which provides masking of synthetic menstrual fluid and discretion.

WO 00/38915 filed Dec. 29, 1999 entitled "Pattern embossed multiplayer microporous films" discloses a multilayer film with first microporous layer having at least 35% filler and second microporous layer having at least 35% filler and a coloring agent. The first and second layer are continuously joined together and have embossed and non-embossed regions wherein the embossed regions color-contrast with the non-embossed regions.

However, all those techniques are rather complex and thus expense. Furthermore, they tend to require materials with high basis weight due to the need for several layers, which generally is disliked in a light, highly flexible absorbent article.

Thus, it is a further objective of the present invention to provide multicolored absorbent articles, which are thin, light and highly flexible due to use of thin materials with low basis weight.

These articles should at the same time provide an attractive outer appearance, provide improved freedom of movement and increased comfort for the wearer and allow the use of economical attractive materials.

SUMMARY OF THE INVENTION

The present invention provides disposable articles selected from baby diapers, pull-on diapers, pants or adult incontinence diapers comprising a liquid pervious topsheet, a liquid impervious backsheet and an absorbent core positioned between the topsheet and the backsheet, wherein the backsheet comprises at least one polymeric film and at least one nonwoven web, the polymeric film and the nonwoven web each have two major surfaces and the polymeric film and the nonwoven web both comprise a polymeric material, at least one of the polymeric materials of the film or of the nonwoven web is colored by pigments comprised within the polymeric material and wherein at least one of the polymeric film or the nonwoven web has visually discernible ornamental designs, the designs being provided by printing a pigmented ink onto at least one of the major surfaces of at least one of the polymeric film or the nonwoven web and the polymeric film being joined in an overlaying region across at least part of one of its major surfaces to at least part of an adjacent major surface of the nonwoven web to form the backsheet and wherein the backsheet in the overlaying region has a L Hunter value on the Hunter scale for darkness/lightness-appearance from about 10 to about 75, an "a" value for red/green-appearance from about −50.0 to about +50.0 and an "b" value for yellow/blue-appearance from about −50.0 to about +50.0 in the areas outside the printed ornamental designs.

DETAILED DESCRIPTION OF THE INVENTION

As used herein, the following terms have the following meaning:

"Absorbent article" refers to devices that absorb and contain liquid, and more specifically, refers to devices that are placed against or in proximity to the body of the wearer to absorb and contain the various exudates discharged from the body. Absorbent articles of the present invention include baby diapers, pull-on diapers, pants or adult incontinence diapers.

"Disposable" is used herein to describe articles that are generally not intended to be laundered or otherwise restored or reused i.e., they are intended to be discarded after a single use and, preferably, to be recycled, composted or otherwise disposed of in an environmentally compatible manner.

"Baby diapers", "pull-on diapers", "pants" and "adult incontinence diapers" refer to absorbent articles generally worn by infants or incontinent persons about the lower torso.

"Attached" or "Joined" encompasses configurations whereby an element is directly secured to another element by affixing the element directly to the other element, and configurations whereby an element is indirectly secured to another element by affixing the element to intermediate member(s) which in turn are affixed to the other element.

"Comprise," "comprising," and "comprises" is an open ended term that specifies the presence of what follows e.g. a component but does not preclude the presents of other features, elements, steps or components known in the art, or disclosed herein.

The disposable absorbent articles of the present invention generally comprise the same features as the baby diapers, pull-on diapers, pants or adult incontinence diapers known in the art. The absorbent article comprises a chassis, which makes up the main body of the absorbent article. The chassis comprises an outer covering including a liquid pervious topsheet and a liquid impervious backsheet. The chassis may also include most or ail of the absorbent core encased between the topsheet and the backsheet. The chassis preferably further includes leg cuffs, waist features and/or side panels. The leg cuffs, side panels and/or the waist feature may comprise elastic members. The front end portion of the absorbent article is configured as the front waist region with the outer edge being the front waist edge. The opposite rear end portion is configured as the rear waist region of the absorbent article with the outer edge being the rear waist edge. An intermediate portion of the absorbent article is configured as the crotch region, which extends longitudinally between the front and rear waist regions. The crotch region is that portion of the absorbent article which, when the absorbent article is worn, is generally positioned between the wearer's legs. The waist regions may include a fastening system comprising fastening members preferably attached to the rear waist region and a landing zone attached to the front waist region. The absorbent article has a longitudinal axis and a transverse axis. The periphery of the absorbent article is defined by the outer edges of the absorbent article in which the longitudinal edges run generally parallel to the longitudinal axis of the absorbent article and the end edges ran generally parallel to the transverse axis of the absorbent article.

The topsheet may comprise a wide variety of materials and configurations well known in the art for disposable absorbent articles.

The absorbent core generally is disposed between the topsheet and the backsheet. The absorbent core may comprise any absorbent material, which is generally compressible, conformable, non-irritating to the wearer's skin, and capable of absorbing and retaining liquids such as urine and other certain body exudates. The absorbent core may comprise a wide variety of liquid-absorbent materials commonly used in disposable absorbent articles and other absorbent articles. The absorbent core comprises a rear and the front core edge, which ran generally parallel to the transverse axis of the absorbent article. In a preferred embodiment of the present invention, the absorbent article is a light, thin absorbent article wherein the distance between the rear core edge and the rear waist edge is at least 40 mm, more preferably at least 45 mm and most preferably at least 50 mm.

The absorbent article may also include other features known in the art including front and rear ear panels, waist cap features, elastics and the like to provide better fit, containment and aesthetic characteristics.

Absorbent articles according to the present invention may be provided with re-closable fastening system or may alternatively be provided in the form of unitary absorbent articles, such as pull-on absorbent articles or pant-type absorbent articles.

The fastening system is preferably comprised by the waist regions and ensures that the absorbent article is kept in place about the wearer. The fastening system may comprise fastening members, which are preferably attached to the rear waist region. In a preferred embodiment the fastening system further comprises a landing zone attached to the front waist region. The fastening member is attached to the front waist region, preferably to the landing zone to form leg openings and a waist opening.

The backsheet is generally the portion of the absorbent article positioned with the absorbent core between the backsheet and the topsheet. The backsheet may be joined with the topsheet. The backsheet prevents the exudates absorbed by the absorbent core and contained within the article from soiling other external articles that may contact the absorbent article, such as bed sheets and undergarments. The backsheet is impervious to liquids (e.g., urine) and comprises a laminate of at least one nonwoven and at least one polymeric film such as a thermoplastic film. The polymeric film preferably has a thickness from about 0.008 mm to about 0.060 mm, more preferably from about 0.010 mm to about 0.040 mm and even more preferably from about 0.010 mm to about 0.020 mm. The polymeric film may be breathable or non-breathable, thus the backsheet may be breathable or non-breathable.

Preferably the backsheet has a basis weight from about 17 gsm to about 125 gsm (grams per square meter), more preferably from about 20 gsm to about 70 gsm and even more preferably from about 20 gsm to about 40 gsm, wherein the polymeric film, has a basis weight from about 10 gsm to about 60 gsm, more preferably from about 10 gsm to about 30 gsm and even more preferably from about 10 gsm to about 20 gsm, and the nonwoven web has a basis weight from about 7 gsm to about 65 gsm, more preferably from about 10 gsm to about 40 gsm and even more preferably from about 10 gsm to about 20 gsm.

The polymeric film of the present invention may be produced from different types of thermoplastic polymers, preferably polyolefins and the copolymers of poly olefins. The polymeric film may be formed by coextrusion processes well known in the art. An inorganic filler (e.g. titanium dioxide) and the thermoplastic polymer are blended together to form a homogeneous mixture in a suitable mixing extruder, or in a separate preliminary compounding step.

Suitable polyolefins include polyethylenes (PE), such as linear low density polyethylene (LLDPE), low density polyethylene (LDPE), ultra low density polyethylene (ULDPE), high density polyethylene (HDPE), or polypropylene (PP) and blends thereof. The mixture is then cast or blown into a film. In embodiments, where the polymeric film comprises different polyolefins, the different polyolefins may be comprised within the polymeric film in different layers or may be coextruded to form a single blended layer. In a preferred embodiment of the present invention, the polymeric film is a coextruded multilayer film comprising PE, PP and copolymers.

Nonwoven webs can be formed by many processes well known in the art such as meltblowing, spunbonding, carded. The fibers of the nonwoven web may be staple or continuous filaments or be formed in situ.

The nonwoven webs according to the present invention may comprise fibers made by nature (natural fibers), made by man (synthetic or man-made), or combinations thereof. Example synthetic fibers, which are derived from natural fibers, include but are not limited to rayon and lyocell, both of which are derived from cellulose, a natural polysaccharide fiber. Synthetic fibers, which are not derived from natural fibers, can be derived from other natural sources or from mineral sources. Example synthetic fibers not derived from natural sources include but are not limited to polysaccharides such as starch. Example fibers from mineral sources include but are not limited to polyolefin fibers such as polypropylene, polyethylene fibers and polyester, which are derived from petroleum, and silicate fibers such as glass and asbestos. However, the nonwoven web of the present invention has to comprise at least some fibers, which are thermoplastic.

The nonwoven web may comprise several layers, wherein each layer may comprise the same polymers or may comprise different polymers in different layers. For example, the nonwoven web may comprise a spunbond layer (made by a spunbond process), a meltblown layer (made by a meltblown process) and a further spunbond layer (spunbond-meltblown-spunbond, so called SMS nonwoven web). Other examples are SSS-(three spunbond layers) or SM-(one spunbond layer and one meltblown layer) nonwoven webs.

The polymeric film is preferably joined to the nonwoven web by lamination processes well known in the art, for example by adhesive lamination, thermo-bonding or extrusion-lamination.

The polymeric film and the nonwoven web both have two major surfaces: One garment-facing surface and one body-facing surface. In a preferred embodiment of the present invention, the garment-facing surface of the polymeric film is joined to the body-facing surface of the nonwoven web. Thus, the nonwoven web is comprised by the garment-facing layer of the backsheet laminate in the absorbent article and is making up the outermost cover of the absorbent article. The polymeric film is comprised by the body-facing layer of the backsheet laminate in the absorbent article.

In one embodiment of the present invention the nonwoven web comprised by the backsheet laminate covers all or substantially all of the garment facing surface of the polymeric film to provide the absorbent article with a cloth-like look and feel. In an alternative embodiment the nonwoven web may cover only discrete predetermined portions.

In one embodiment of the present invention, the backsheet comprises a color-pigmented, polymeric film with visually discernible ornamental designs printed on at least one of the two major surfaces of the polymeric film, the nonwoven web or both.

In an alternative embodiment of the present invention, the backsheet comprises a color-pigmented nonwoven web with visually discernible ornamental designs printed on at least one of the two major surfaces of the polymeric film, the nonwoven web or both.

In still another embodiment of the present invention, the backsheet comprises a color-pigmented polymeric film and a color-pigmented nonwoven web with visually discernible ornamental designs printed on at least one of the two major surfaces of the polymeric film, the nonwoven web or both.

In any of these embodiments, the designs are preferably printed on the garment-facing surface of the nonwoven web and/or polymeric film.

Furthermore, in any of these embodiments, the polymeric film may be joined to the nonwoven web before or after the designs have been printed on the polymeric film, on the nonwoven web or on both.

Color-Pigmentation

The coloring agent used to color-pigment the nonwoven web and/or the polymeric film of the present invention is preferably added before melting the thermoplastic material comprised by the nonwoven web and/or polymeric film. Alternatively, the coloring agent is added after the thermoplastic polymers, which form the polymeric film and/or nonwoven web, are molten but before the polymeric film is formed by extrusion respectively before the fibers of the nonwoven web are formed and the nonwoven web is manufactured.

The coloring agents may be generally termed as pigments, referring to insoluble color matter used in finely dispersed forms. The pigments may be dyes, organic pigments or inorganic pigments. Exemplary organic pigments may include: C. I. Pigment Yellow 1, C. I. Pigment Yellow 3, C. I. Pigment Yellow 13, C. I. Pigment Red 5, C. I. Pigment Red 7, C. I. Pigment Red 12, C. I. Pigment Red 112, C. I. Pigment Red 122, C. I. Pigment Blue 1, C. I. Pigment Blue 2, C. I. Pigment Blue 16, C. I. Vat Blue 4, C. I. Vat Blue 6, or Carbon black. Exemplary inorganic pigments may include: titanium dioxide (e.g., Pigment White 6), carbon black (e.g., Pigment Black 7), iron oxides, ferric oxide black (e.g., Pigment Black 11), chromium oxide, or ferric ammonium ferrocyanide. Exemplary dyes may include: Solvent Yellow 14, Dispersed Yellow 23, Metanil Yellow, Solvent Red 111, Dispersed Violet 1, Solvent Blue 56, Solvent Orange 3, Solvent Green 4, Acid Red 52, Basic Red 1, Solvent Orange 63, or Jet Black. The different pigments may be used in any combination and ratio. Alternatively, only one pigment may be applied. Based upon weight of the polymeric material, the suitable addition range for the total amount of coloring agent may be from about 0.1% to about 49%, preferably from about 3% to about 30% more preferably from about 5% to about 20%.

In a preferred embodiment of the present invention, an inorganic or organic filler (e.g. titanium dioxide) is added together with at least one second color pigment. Due to the titanium dioxide, the resulting polymeric film or nonwoven web gets a certain degree of opacity. Alternatively, instead of or additionally to titanium dioxide, calcium carbonate may be used as "whitener" to ensure opacity. Calcium carbonate also adds a certain degree of breathability, which may be especially desirable in polymeric films. In the case of breathable films, the extruded polymeric film is stretched at least in one direction to impart breathability to at least a part of the film.

Preferably, the amount of titanium dioxide in the polymeric film is from about 0.5% by weight to about 5% by weight, more preferably, the amount is from about 0.5% by weight to about 3% by weight and even more preferably, the amount is from about 0.5% by weight to about 2.5% by weight. However, in exceptional cases, the amount of titanium dioxide in the polymeric film may be even up to 10% by weight.

The amount of Calcium carbonate is different in breathable polymeric films compared to non-breathable polymeric films, because it strongly adds to breathability. In non-breathable polymeric films the amount of calcium carbonate is preferably from about 5% by weight to about 40% by weight, more preferably from about 5% by weight to about 30% by weight. In breathable polymeric films, the amount of calcium carbonate is preferably from about 40% by weight to about 80% by weight, more preferably from about 45% by weight to abut 65% by weight.

Preferably, the amount of titanium dioxide or calcium carbonate in the nonwoven web is from about 0.1% by weight to about 2.0% by weight, more preferably from about 0.1% by weight to about 1.5% by weight. However, the use of titanium dioxide is preferred over the use of calcium carbonate.

Besides the coloring agents other additives may be applied for manufacturing the polymeric film, e.g. anti-oxidants, UV inhibitors, process aids such as slip agents like silicone.

Printing

According to the present invention, the backsheet is provided with visually discernible ornamental designs. These designs may either be printed on the polymeric film, on the nonwoven web or on both. The designs may be in the form of animals, flowers, toys, graphics, like dots or stars, or any other appealing shape. The designs may comprise a number of different shapes and colors or may, alternatively, comprise only one design. Moreover, they may be of any size applicable. Only one or a small number of the designs may be applied on each backsheet. Alternatively, the designs may be applied in multiple copies on each backsheet. "Visually Discernible" according to the present invention means that the designs are visible to the naked eye, without the need to apply any auxiliary devices like microscopes or the like (except for common spectacles).

The ink composition of the present invention is any liquid composition, which may be printed Onto the nonwoven web or polymeric film.

Components of the ink composition of the present invention may include but are not limited to: a vehicle such as a solvent or water; a colorant such as a pigment; a binder; and other components which may include but are not limited to wax, crosslinking agents, pH control agents, viscosity modifiers, defoamers, dispersants, printing press hygiene control agents, preservatives, and corrosion control agents.

As used herein, "ink" refers to any liquid composition or components thereof applied to the nonwoven web and/or polymeric film and which remains thereon in a visible pattern even though components of the ink may evaporate. The components of the ink composition may be applied to the nonwoven web and/or polymeric film sequentially or as a mixture. As used herein, "vehicle" refers to the liquid component of the ink composition utilized to convey the ink composition to the surface of the nonwoven web and/or polymeric film. As used herein, "pigment" refers to insoluble color matter used in finely divided dispersed form to impart color to the ink. As used herein, "binder" refers to the adhesive component of the ink composition. The same ink may be used for printing nonwoven webs and for printing polymeric films.

Though the pigments described and used herein for printing the ornamental designs are organic pigments, it is understood that the ink compositions of the present invention could be extended to include inorganic pigments as well as other organic pigments. Smaller pigment particle sizes are preferred over relatively larger size pigment particles. The pigment of the present invention preferably has a particle size of less than 5 microns, more preferably less than 1 micron, and even more preferably less than 0.5 microns.

Ink is applied to the nonwoven web and/or polymeric film by printing the ink onto the nonwoven web and/or polymeric film.

Printing processes suitable for this invention include but are not limited to: lithography, letterpress, gravure, screen printing, intaglio and preferably flexography. According to the present invention, a further suitable printing process is ink jet printing, which is a non-contact printing technique, wherein the ink is applied in small droplets. A single color image or multi-color image may be applied to the nonwoven web and/or polymeric film.

When a single color is applied on a white surface, it is possible to vary the intensity of this color e.g. by varying the add-on level of color per surface area (e.g. by varying the density of ink dots per surface area in a halftone process). It is thus possible to produce different shades of one color. It is, however, not possible to produce the effect of an additional second color by varying the add-on level on white surfaces.

Contrary, in the present invention it is possible to produce the effect of additional colors due to the color-pigmented surface whereon the ornamental designs are printed. For example, when non-transparent, opaque blue ink is printed on a yellow surface without covering the whole surface (e.g. by allying small, discrete dots in a halftoning-process), the such treated surface will be visually perceived as being green. When the same opaque blue ink is applied such, that the whole surface is completely covered, the surface will be visually perceived as being blue. Thus, by covering at least a first area of a surface with opaque ink in a halftoning process while covering at least a second area completely with the same ink, the effect of an additional color is created. Moreover, by varying the grid pattern of the halftoning process it is also possible to vary the shades and intensities of these colors.

As used herein, "percent dot coverage" refers to the amount of a specified print area covered by halftoning dots in relation to the total specified print area. In the present invention, the percent dot coverage is preferably between 3% and 90%, more preferably between 10% and 80%. Furthermore, the frequency, size or combination thereof of halftone dots may be varied broadly.

Alternatively to applying opaque colors in a halftoning process, it is also possible to use transparent inks, which are also within the scope of this invention. When using transparent ink, the thickness of the ink on the surface is varied to produce the effect of a third color. E.g. when transparent blue ink is applied in a thin layer on a yellow surface, the yellow surface is partially shining through such, that color will be visually perceived as being green. When the transparent blue ink is applied in a relatively thick layer on the yellow surface, almost none of the yellow color will be shining through any more, such that the color will be visually perceived as being blue. Thus, by covering at least a first area of a surface with a relatively thin layer of transparent ink while applying a relatively thick layer of the same ink in at least a second area of the surface, the effect of an additional color is created.

Moreover, the same effects can be achieved by printing e.g. two different colors in a halftoning process in the same area, such that a mixture of dots of at least two different colors is applied. When using transparent ink, e.g. two different colors may be printed, overlying each other and wherein the add-on level of these inks is varied to created the effect of additional colors and different shades. However, when applying this technique on a color pigmented polymeric film or nonwoven web, the "background" color can be used, which enables vivid, multicolored ornamental designs on polymeric films and/or nonwoven webs without the need for multiple colors. This simplifies the printing process, which enables fast and inexpensive printing. In a preferred embodiment of the present invention, two different colors are applied to print the visible discernible ornamental designs.

When the ornamental designs are printed on the polymeric film or on the nonwoven web comprised by the backsheet, the designs preferably do not comprise more than 50% of the total surface of at least one of the two major surfaces of the backsheet. More preferably, the ornamental designs do not comprise more than 40%, still more preferred not more than 30% and most preferred not more than 20% of at least one of the two major surfaces of the backsheet.

In a preferred embodiment of the present invention, more than 60% of the ornamental designs printed on the polymeric film and/or the nonwoven web of the backsheet coincide with the area of the backsheet, which is covered by the absorbent core, more preferably more than 70%, still more preferably more than 80% and most preferred more than 90%. Thereby, the masking effect of the ornamental designs is improved with respect to stains formed by urine or other exudates disposed in the absorbent article.

The ornamental designs may be printed, on either of the two major surfaces of the polymeric film and/or the nonwoven web. When the ornamental designs are printed on the polymeric film, they are preferably applied on the garment-facing surface of the film to avoid direct contact between the ink and the liquids and other exudates disposed in the absorbent article. Alternatively, the ornamental designs may be applied on the body-facing surface of the polymeric film. When the ornamental designs are printed on the nonwoven web, they may be printed on the body-facing surface or, more preferably, on the garment facing surface of the nonwoven web.

To improve the printing capability of the nonwoven web or polymeric film, the nonwoven web or polymeric film may undergo a corona treatment prior to printing the ornamental designs.

L Hunter Value and "a" and "b" Values of the Backsheet

The L Hunter value as well as the "a" and "b" values are measured in the area outside the ornamental designs, thus these values are measured for the color-pigmented area of the backsheet without comprising the printed area. Furthermore, the L Hunter value and the "a" and "b" values are measured in the area, where the polymeric film is covered by the nonwoven web. Preferably, the L Hunter value and the "a" and "b" values are measured on the garment-facing surface of the backsheet and thus on the surface, where the nonwoven web is facing the viewer. Alternatively, the L Hunter value and the "a" and "b" values are measured on the body-facing surface of the backsheet and thus on the surface, where the polymeric film is facing the viewer.

The L Hunter scale values, utilized herein to define the darkness/lightness of the backsheet according to the present invention, are units of color measurement in the Hunter Color system. A complete technical description of the system can be found in an article by R. S. Hunter, 'photoelectric color difference Meter', Journal of the Optical Society of America, Vol. 48, pp. 985-95, 1958. Devices specially designed for the measurement of color on the Hunter scales are described in U.S. Pat. No. 3,003,388 to Hunter et al., issued Oct. 10, 1961. In general, Hunter Color "L" scale values are units of light reflectance measurement, and the higher the value is, the lighter the color is since a lighter colored material reflects more light. In particular, in the Hunter Color system the "L" scale contains 100 equal units of division, absolute black is at the bottom of the scale (L=0) and absolute white is at the top of the scale (L=100). Thus in measuring Hunter Color values of the materials used in the absorbent articles according to the present invention, the lower the "L" scale value, the darker the material.

The backsheet herein might be of any color provided that the L Hunter value and the "a" value and "b" value defined herein are meet.

'Color' as referred to herein include any primary color, i.e. black, white, red, blue, violet, orange, yellow, green, and indigo as well as any declination thereof or mixture thereof.

Colors can be measured according an internationally recognized 3D solid diagram of colors where all colors that are perceived by the human eye are converted into a numerical code. This system is based on three dimensions (x,y,z) and specifically L, a, b.

When a color is defined according to this system L represents lightness (0=black, 100=white), a and b independently each represent a two color axis, a representing the axis red/green (+a=red, −a=green), while b represents the axis yellow/blue (+b=yellow, −b=blue).

Any color is identified by a unique ΔE value, which is mathematically expressed by the equation:

$$\Delta E = [(L\text{ref.} - L\text{sample})2 + (a\text{ref.} - a\text{sample})2 + (b\text{ref.} - b\text{sample})2]^{1/2}$$

ΔE represents graphically the distance between the reference color and the no color point (i.e. center of sphere Lref=50, aref=0, bref=0) of the 3D model.

Color can be measured using the colorimeter MINOLTA mode CR-300 instrument (available from the Minolta Company, Japan) which provides the coordinates L, a, b and from which the ΔE value can be determined.

According to the present invention the backsheet of the absorbent articles has a L Hunter value from about 10 to about 75, more preferably from about 10 to about 65, and still more preferably from about 15 to about 60.

Moreover, the backsheet according to the present invention has an "a" value from about −50.0 to about +50.0, more preferably from about −30.0 to about +30.0, even more preferably from about −20.0 to about +20.0 and most preferred from about −10.0 to about +10.0. Furthermore, the backsheet according to the present invention has a "b" value from about −50.0 to about +50.0, more preferably from about −35.0 to about +25.0, even more preferably from about −25.0 to about +15.0 and most preferred from about −20.0 to about +5.0.

In the present invention the L Hunter values as well as the "a" and "b" values refer to the values for a single layer of the backsheet material and thus not for several layers of the materials folded upon itself. While carrying out the measurements of the values, the backsheet materials are placed directly on a white background.

A backsheet, which is colored such, that it fulfills the above defined L Hunter value and the a and b values defined above provides a vivid, shining color. The backsheet further provides improved masking effects, even if the polymeric film and/or the nonwoven web comprised by the backsheet have reduced opacity. This facilitates the use of smaller amounts of whiteners like titanium dioxide in the polymeric film and therefore enables reduction of costs while at the same time providing superior absorbent articles.

Opacity

The opacity of the backsheet of the present invention is preferably from about 55% to about 100%, more preferably from about 55% to about 95% and even more preferred from about 55% to about 80% and most preferred from about 60% to about 70%. According to the present invention opacity is measured in the area, where the polymeric film is covered by the nonwoven web. Preferably, the opacity is measured on the garment-facing surface of the backsheet and thus on the surface, where the nonwoven web is facing the viewer. Alternatively, the opacity is measured on the body-facing surface of the backsheet and thus on the surface, where the polymeric film is facing the viewer. Moreover, opacity is measured in the area outside the ornamental designs, thus for the color-pigmented area of the backsheet without comprising the printed area. The opacity is measured by the following test method:

Method to determine the opacity:

Opacity is measured according to the method described in detail in WO 01/49230, starting on page 19, and essentially follows the following description:

Apparatus and Materials

BYK-Gardner TCS® Color Sphere Spectrophotometer, which is a spectrophotometer using a d/8° geometry (diffuse illumination and 8° viewing), with instrument operation manual and software; available from BYK-Gardner, Inc., Columbia, Md. U.S.A.

Menu driven quality control software program; available from BYK-Gardner, Inc.

Small area lens and aperture; available from BYK-Gardner, Inc.

Quartz halogen lamp with infrared filter; available from BYK-Gardner, Inc.

Black cavity; available from BYK-Gardner, Inc.

White Japanese opal standard, with calibration data; available from BYK-Gardner, Inc.

Cutting device, such as a scissors or paper cutter capable of cutting specimens to the requisite dimensions as specified below.

Conditioning: Testing should be conducted in a standard laboratory atmosphere of 23°+2° C. (73.4°+3.6° F.) and 50%+5% relative humidity.

Test Specimen: For each material to be tested, cut five specimens of approximately 51 by 51 millimeters (2 by 2 inches).

Preparation of Apparatus and Materials: For general operation procedure see operation manual of the Color Sphere Spectrophotometer The setting configuration should be as follows:
Color Scale
Display: XYZ
Illuminant: C
Observer: 2°

Calibration: Calibrate with Black cavity and Japanese opal standard tile. Place the tile so that the 2 pegs are resting on top of the reflectance port cover plate.

Compare the nanometer results to the number supplied by BYK-Gardner for that tile. Nanometer numbers for 380, 540, and 720 nm must be +0.25 nanometer. If the result is greater than +0.25 nm, repeat the calibration.

Use Opacity mode: White under standard and sample. The opacity measurement consists of measurement of a specimen backed with a black reference and the measurement of the same specimen backed with a white reference. The Color measurement of the specimen can be displayed with either the black reference or the white reference as the backing. Select "display white" for the Sample and Standard columns.

Procedure

1. Center a single specimen over the reflectance port making sure there are no wrinkles and do not use areas with printed ornamental designs.
2. Back the specimen with the black cavity.
3. Place the white reference (white side of black cavity) over the specimen on the reflectance port. Do not move the specimen test area between the black cavity reading and the white reference reading.
4. Record the C2° Opacity result.

Repeat 1. to 4. for each specimen.

Report:

The opacity values in percent are reported.

All documents cited in the Detailed Description of the Invention are, in relevant part, incorporated herein by reference; the citation of any document is not to be construed as an admission that it is prior art with respect to the present invention.

While particular embodiments of the present invention have been illustrated and described, it Would be obvious to those skilled in the art that various other changes and modifications can be made without departing from the spirit and scope of the invention. It is therefore intended to cover in the appended claims all such changes and modifications that are within the scope of this invention.

What is claimed is:

1. A disposable article selected from baby diapers, pull-on diapers, pants or adult incontinence diapers comprising a liquid pervious topsheet, a liquid impervious backsheet and an absorbent core positioned between said topsheet and said backsheet, wherein said backsheet comprises at least one polymeric film and at least one nonwoven web formed of fibers, wherein said polymeric film and said nonwoven web each have two major surfaces, said polymeric film comprises a polymeric film material, and said nonwoven web fibers comprise a polymeric nonwoven web material, wherein at least one of said polymer film material or said polymeric nonwoven web material is color-pigmented by one or more pigments mixed thereinto prior to formation of said polymeric film or said nonwoven web, and wherein at least one of said polymeric film or said nonwoven web has visually discernible printed designs, said printed designs being provided by printing an ink onto at least one of said major surfaces of at least one of said polymeric film or said nonwoven web, said polymeric film being joined in an overlaying region across at least part of one of its major surfaces to at least part of an adjacent major surface of said nonwoven web to form said backsheet, wherein said backsheet in said overlaying region has an L Hunter value on the Hunter scale for darkness/lightness-appearance from 10 to 75, an "a" value for red/green-appearance from about −50.0 to about +50.0 and a "b" value for yellow/blue-appearance from about −50.0 to about +50.0 in the areas outside the printed designs.

2. The disposable article according to claim 1, wherein said backsheet in said overlaying region has an opacity from about 55% to about 100% in the areas outside the printed designs.

3. The disposable article according to claim 1, wherein one of said two major surfaces of said polymeric film and said nonwoven web is a garment facing surface and said discernible printed designs are provided by printing on at least one of said garment facing surfaces of said polymeric film or said nonwoven web.

4. The disposable article according to claim 1, wherein said backsheet comprises a garment facing layer and a body facing layer and said nonwoven web is comprised by said garment facing layer and said polymeric film is comprised by said body facing layer.

5. The disposable article according to claim 1, wherein said printed designs comprise not more than about 50% of at least one of the two major surfaces of said backsheet.

6. The disposable article according to claim 1, wherein more than about 60% of said printed designs coincide with the area covered by said absorbent core.

7. The disposable article according to claim 1, wherein said disposable article comprises a rear waist edge and said absorbent core comprises a rear core end edge and wherein the distance between said rear end edge and said rear core end edge comprises at least about 40 mm.

8. The disposable article according to claim 1, wherein said printing is applied such, that the effect of an additional color is created by covering at least a first area of at least one of said major surfaces of at least one of said polymeric film or said nonwoven web with opaque ink in a halftoning process while covering at least a second area completely with the same ink.

9. The disposable article according to claim 1, Wherein said printing is applied such that the effect of an additional color is created by covering at least a first area of at least one of said major surfaces of at least one of said polymeric film or said nonwoven web with a relatively thin layer of a transparent ink while applying a relatively thick layer of the same ink in at least a second area.

10. The disposable article of claim 1, wherein said backsheet in said overlying region has an L Hunter value on the Hunter scale for darkness/lightness-appearance from 10 to 65, in the areas outside the printed designs.

11. The disposable article of claim 1, wherein said backsheet in said overlaying region has an "a" value for red/green-appearance from about −30.0 to about +30.0 and a "b" value for yellow/blue-appearance from about −35.0 to about +25.0, in the areas outside the printed designs.

12. A disposable article selected from baby diapers, pull-on diapers, pants or adult incontinence diapers comprising a liquid pervious topsheet, a liquid impervious backsheet and an absorbent core positioned between said topsheet and said backsheet, wherein said backsheet comprises at least one polymeric film and at least one nonwoven web formed of fibers, wherein said polymeric film and said nonwoven web each have two major surfaces, said polymeric film comprises a polymeric film material, and said nonwoven web fibers comprise a polymeric nonwoven web material, wherein at least one of said polymer film material or said polymeric nonwoven web material is pigmented by titanium dioxide or calcium carbonate mixed thereinto prior to formation of said polymeric film or said nonwoven web, and wherein at least one of said polymeric film or said nonwoven web has visually discernible printed designs, said printed designs being provided by printing an ink onto at least one of said major surfaces of at least one of said polymeric film or said nonwoven web, said polymeric film being joined in an overlaying region across at least part of one of its major surfaces to at least part of an adjacent major surface of said nonwoven web to form said backsheet, wherein said backsheet in said overlaying region has an L Hunter value on the Hunter scale for darkness/lightness-appearance from 10 to 75, an "a" value for red/green-appearance from about −50.0 to about +50.0 and a "b" value for yellow/blue-appearance from about −50.0 to about +50.0 in the areas outside the printed designs.

13. The disposable article according to claim 12, wherein said backsheet said overlaying region has an opacity from about 55% to about 100% in the areas outside the printed designs.

14. The disposable article according to claim 12, wherein one of said two major surfaces of said polymeric film and said nonwoven web is a garment facing surface and said discernible printed designs are provided by printing on at least one of said garment facing surfaces of said polymeric film or said nonwoven web.

15. The disposable article according to claim 12, wherein said backsheet comprises a garment facing layer and a body facing layer and said nonwoven web is comprised by said garment facing layer and said polymeric film is comprised by said body facing layer.

16. The disposable article according to claim 12, wherein said printed designs comprise not more than about 50% of at least one of the two major surfaces of said backsheet.

17. The disposable article according to claim 12, wherein said disposable article comprises a rear waist edge and said absorbent core comprises a rear core end edge and wherein the distance between said rear end edge and said rear core end edge comprises at least about 40 mm.

18. The disposable article according to claim 12, wherein said printing is applied such, that the effect of an additional color is created by covering at least a first area of at least one of said major surfaces of at least one of said polymeric film or said nonwoven web with opaque ink in a halftoning process while covering at least a second area completely with the same ink.

19. The disposable article according to claim 12, wherein said printing is applied such that the effect of an additional color is created by covering at least a first area of at least one of said major surfaces of at least one of said polymeric film or said nonwoven web with a relatively thin layer of a transparent ink while applying a relatively thick layer of the same ink in at least a second area.

20. The disposable article of claim 12, wherein said backsheet in said overlying region has an L Hunter value on the Hunter scale for darkness/lightness-appearance from 10 to 65, in the areas outside the printed designs.

21. The disposable article of claim 12, wherein said backsheet in said overlaying region has an "a" value for red/green-appearance from about −30.0 to about +30.0 and a "b" value for yellow/blue-appearance from about −35.0 to about +25.0, in the areas outside the printed designs.

\* \* \* \* \*